United States Patent [19]

Batchelder et al.

[11] Patent Number: 5,061,070
[45] Date of Patent: Oct. 29, 1991

[54] PARTICULATE INSPECTION OF FLUIDS USING INTERFEROMETRIC LIGHT MEASUREMENTS

[75] Inventors: John S. Batchelder, Tarrytown; Donald M. DeCain, New York; Marc A. Taubenblatt, Tarrytown; Hermantha K. Wickramasinghe, Chappaqua; Clayton C. Williams, Peekskill, all of N.Y.

[73] Assignee: International Business Machines Corporation, Armonk, N.Y.

[21] Appl. No.: 184,639

[22] Filed: Apr. 22, 1988

[51] Int. Cl.$^5$ .............................................. G01B 9/02
[52] U.S. Cl. .................................. 356/345; 356/351; 356/353
[58] Field of Search ................ 356/345, 349, 351, 353

[56] References Cited

U.S. PATENT DOCUMENTS

| | | | |
|---|---|---|---|
| 2,679,183 | 5/1954 | Buchele et al. | 356/353 |
| 3,662,176 | 5/1972 | Kametsky et al. | |
| 3,732,014 | 5/1973 | Uzgiris . | |
| 3,796,495 | 3/1974 | Laub | 356/359 |
| 4,329,054 | 5/1982 | Bachalo . | |
| 4,477,187 | 10/1984 | Pettit et al. | 356/349 |
| 4,577,964 | 3/1986 | Hansen, Jr. . | |

Primary Examiner—Samuel Turner
Attorney, Agent, or Firm—Philip J. Feig

[57] ABSTRACT

A method and apparatus for monitoring process fluids used in the manufacture of semiconductor components and other microelectronic devices relies upon detection of the phase shift of a pair of optical energy beams encountering a bubble or particle in the fluid. The system distinguishes between bubbles and particles having indices of refraction greater than the surrounding fluid and between different types and sizes of particles.

42 Claims, 3 Drawing Sheets

SIGNAL AT PHOTODIODE 54
TIME

SIGNAL AT PHOTODIODE 56
TIME

SUMMATION OF SIGNALS
TIME

SUMMATION OF SIGNALS
TIME

FLUID VOLUME / SEC.
SENSITIVITY

PARTICULATE INSPECTION OF FLUIDS USING INTERFEROMETRIC LIGHT MEASUREMENTS

BACKGROUND OF THE INVENTION

This invention relates to inspection of process fluids used in the manufacture of semiconductor components and other microelectronic devices and specifically relates to particulate inspection of liquids by interferometric light measurements. More particularly, the phase shift of light travelling through a local index perturbation or object in the fluid such as a bubble or particle, is detected and analyzed in order to determine the characteristics and size of the object.

Contamination control in the manufacture of semiconductor components and other microelectronic devices is becoming a process variable. Particulate contamination causes more than half of the yield loss in volume semiconductor manufacturing. A substantial amount of this loss is due to the chemicals, such as solvents, acids and bases and process gases, that come into contact with the wafers. The contaminant concentration in such fluids is typically more than three orders of magnitude greater than that present in clean room air and six orders of magnitude greater than that present in the next generation of clean rooms.

Presently used monitoring techniques for examining process fluids, both liquids and gases, have several major deficiencies that are overcome by the present invention. Currently available devices are unable to discriminate between gas bubbles and particles in a process liquid. These devices lose sensitivity for detecting particles having indices of refraction close to that of the fluid. Also, the inspected volume throughput in the available devices demonstrates a precipitous drop as the particle size threshold is reduced. Moreover, these devices have not demonstrated extendability to the one-tenth groundrule limit for detecting particles. The one-tenth groundrule limit refers to the case in which devices are manufactured, for example, in the one micron range, contaminants must be detectable to one-tenth of the range, or 0.1 micron size.

It is known to detect particles by measuring light scattered from the particles. This technique is effective for particle sizes having a circumference as small as the wavelength of the light, at which point the particles exhibit the characteristic Rayleigh scatter cross section that varies as the sixth power of the particle size. Small particles therefore become difficult to measure. Improving particle size sensitivity by a factor of two requires improving the scattered light detection sensitivity by a factor of 64.

An alternative method for improving particle size sensitivity is to consider the particle as a phase object, and measure the effect of the particle on a wavefront. Placing the particle in one arm of an interferometer achieves the desired measurement. Another technique, the preferred method, is to use bright field analysis as will be described hereinafter. Dark field analysis is another alternative technique for measuring the phase shift of the scattered light.

SUMMARY OF THE INVENTION

In accordance with the present invention, detection and analysis of the phase shift of the light enables differentiation between bubbles and particles. It has been observed, using the preferred method that detected signals for a bubble and a particle are 180 degrees out-of-phase thereby enabling classification of an object in a liquid as either a bubble or a particle. Moreover, signal analysis of the detected signal enables differentiation of the size and type of particle, i.e. metal, dielectric, bacteria, and the like.

Conventional monitoring techniques exhibit Johnson noise limited sensitivity. The present invention removes the Johnson noise limitation resulting in the sensitivity being limited by only the shot noise of the optical beam.

In the present arrangement, the phase shift is measured from the front of the particle, i.e. in substantially the same direction as the incident optical beam. It is essential, however, that the incident optical beam is focused at the location of the object in the fluid, otherwise the object will not be detected. An incident optical beam upon encountering an object or local index perturbation in a fluid will change velocity when passing through the object. The magnitude and the increase or decrease in velocity is dependent upon the characteristics and size of the object. The change in velocity results in a phase shift of the optical beam.

A principal object of the present invention is, therefore, the provision of a method of inspecting a fluid for objects by detection and analysis of the phase shift of an optical beam encountering an object.

Another object of the invention is the provision of a particle monitor for detecting and analyzing the phase shift of an optical beam encountering a particle.

A further object of the invention is the provision of two optical optical beams traveling along the same optical path everywhere except at the sample volume in the fluid.

Further and still other objects of the present invention will become more clearly apparent when the following description is read in conjunction with the accompanying drawings.

DETAILED DESCRIPTION

Figure 1:
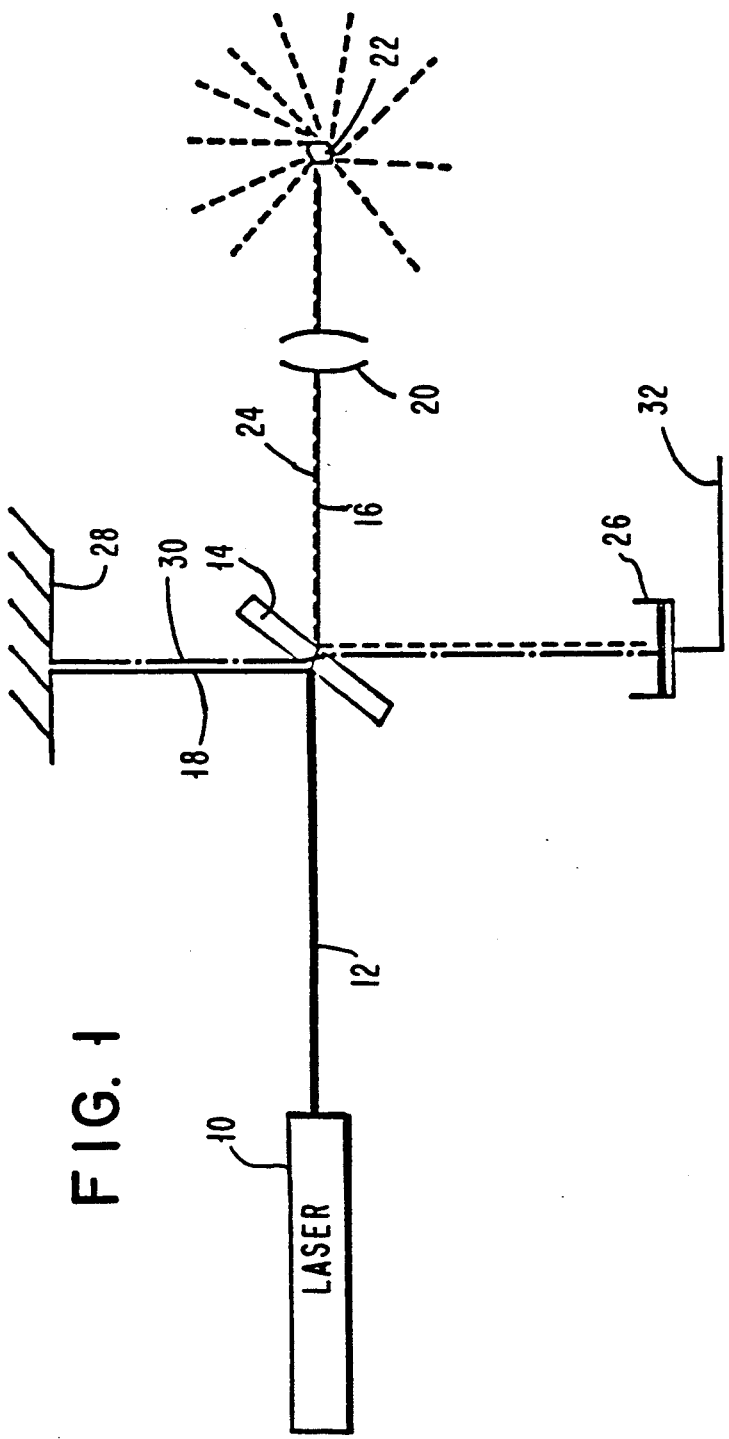
FIG. 1 is a schematic representation of a known interferometric optical beam particle detector.

Referring now to the figures, and to FIG. 1 in particular, there is shown schematically an interferometric particle detector. A laser 10 transmits a beam of light 12 towards a beam splitter 14 where the beam is split into a sample beam 16 and a reference beam 18. The sample beam travels through an objective lens 20 to a scatterer or particle 22 to be detected at one arm of the interferometer. The incident optical beam is scattered in all directions by the particle as indicated by the dashed lines, including line 24 which is a portion of the scattered light traveling back through lens 20 to beam splitter 14 whereat the beam is reflected to a detector 26.

The reference beam 18 travels from beam splitter 14 towards a mirror or reflector 28 located at the other arm of the interferometer where the beam is reflected along the path of broken line 30, through the beam splitter 14 to detector 26. The detector 26 may be a photodetector, a photo multiplier tube or any other detector well known in the art for receiving a reference beam and a sample beam and providing an output signal along a conductor 32 commensurate with the intensity of the reflected beam 24 i.e. the volume of the particle 22.

In the arrangement shown in FIG. 1, only the sample beam travels to the scatterer containing fluid while the reference signal traverses a totally different path. The result is a signal along conductor 32 which exhibits a relatively low signal-to-noise ratio if the particle remains in the optical beam for ten second or longer.

The present invention concerns transmitting two parallel beams of optical energy into a fluid to be inspected. The two parallel beams are mutually coherent prior to entering the fluid, of different polarizations, laterally displaced and focussed in the fluid in a focal plane which plane is normal to the beam axes. The beams exhibit a depth of focus equal to the vacuum wavelength multiplied by the index of refraction of the fluid divided by twice the square of the numerical aperture of the illuminating optics which is centered about the focal plane. After passing through the focal plane a distance greater than the depth of focus, the two beams are coherently interfered at at least one detector. Coherently interfered refers to causing the two beams to be substantially coaxial at the detector. A signal is generated commensurate with the difference of the phases of each beam at the detector. Subsequent signal analysis is performed upon the generated signal to determine the characteristics of any object detected in the fluid. An absence of a detected object results in a substantially zero phase shift difference between the two beams.

Figure 2:
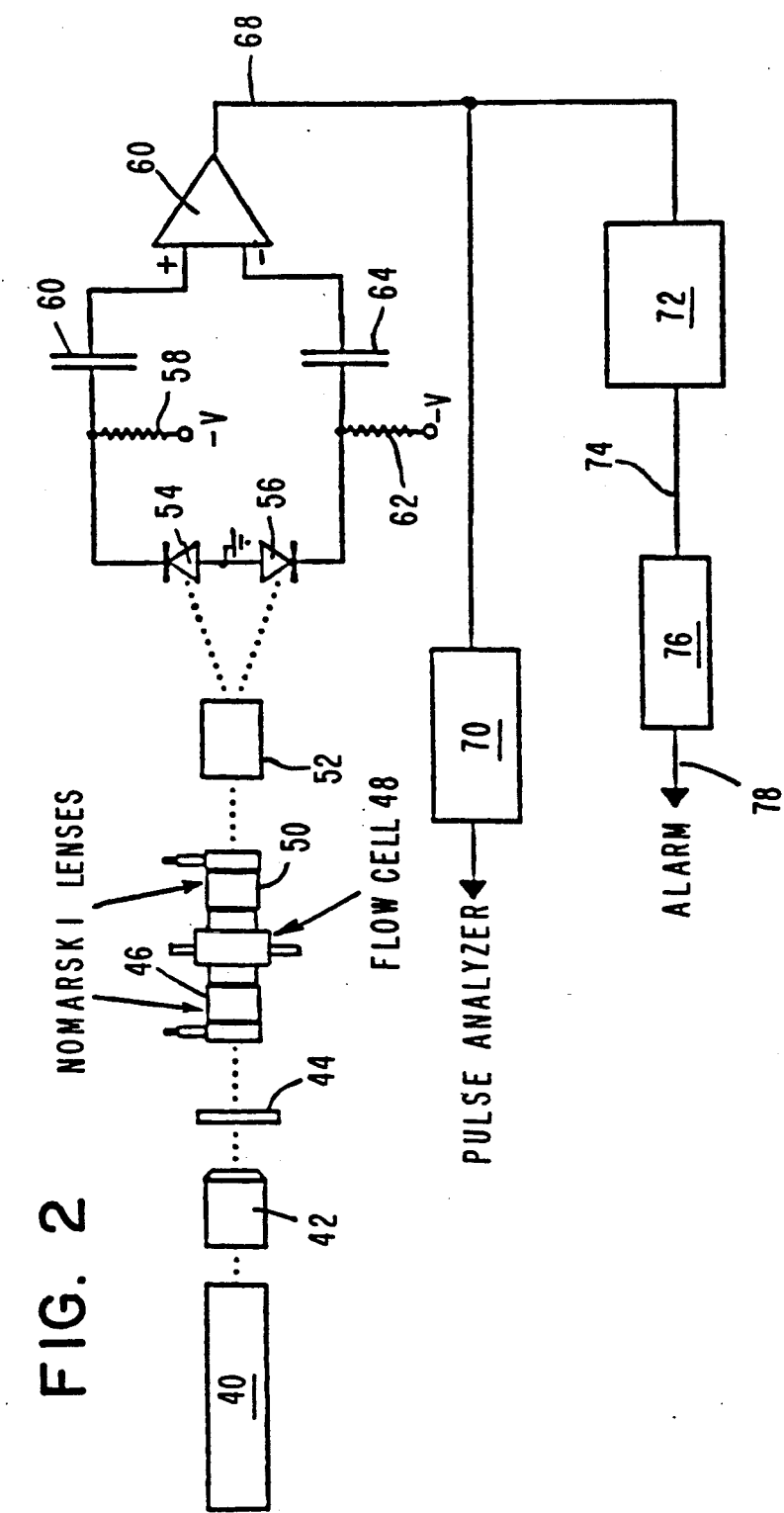
FIG. 2 is a schematic representation of a preferred embodiment of the invention.

FIG. 2 is a schematic representation of a preferred embodiment for practicing the present invention. A laser 40 is preferably an array of single GaAs lasers, although other types of lasers such as HeNe, argon-ion, krypton, pulsed CW, and even infrared lasers will perform acceptably. The laser 40 transmits a laser energy beam through a beam expander 42 and quarter-wave plate 44. The beam then enters a commercially available Nomarski objective 46 where the incident circularly polarized energy beam is split into two beams. One beam is polarized in a direction normal to the plane of the drawing and the other beam is polarized in a direction orthogonal to the first beam. The two beams, whose optical axes are offset from each other by a lateral displacement, enter a liquid flow cell 48. The lens 46 is disposed so that the waist of the beam, i.e. the focal point, is located in the liquid flow cell in a plane normal to the axes of the beams.

In operation, the fluid to be monitored flows through the flow cell 48 where the dual beams traverse the fluid and interact with any objects such as bubbles or particles in the fluid. It is also possible to direct the fluid flow to pass through the focal region of both spot beams thereby providing a bipolar signal that can be detected in the presence of noise.

After traversing the flow cell 48, the two orthogonally polarized beams pass through another Nomarski lens 50 whereat the two beams are recombined into a single circularly polarized beam. The beam then enters a commercially available Wollaston prism 52 which separates the beam into two beams, one at a plus 45 degree angle and the other at a minus 45 degree angle causing the polarization directions of the two beams to be orthogonal to each other. Each beam is received at a respective photodiode 54, 56 or equivalent detector. The detection circuit shown uses differential photodiodes 54 and 56 in order to cancel laser noise by means of common mode rejection provided by amplifier 66.

In order to provide a better understanding of the detection circuitry, the mathematical relationship of the two beams, excluding time dependent factors, exiting from Wollaston prism 52 will be explained. In bright field analysis of the type illustrated in FIG. 2, a linearly polarized laser beam is generated according to the equation:

$$E = \frac{\hat{x} + \hat{y}}{\sqrt{2}} Ei$$

where x is the polarization along the x-axis, y is the polarization along the y-axis and Ei is the incident energy beam.

After passing through quarter-wave plate 44, the circularly polarized energy beam is represented by:

$$E = \frac{\hat{x} \exp[i\pi/2] + \hat{y}}{\sqrt{2}} Ei$$

The first Nomarski objective 46 splits the incoming circularly polarized beam into two spots of mutually orthogonal linear polarization at the focal region on the flow cell 48, and the second Nomarski objective 50 recombines the two beams into a single circularly polarized beam according to the equation:

$$E = \frac{\hat{x} \exp[i\pi/2 + i\Delta\phi'] + \hat{y}}{\sqrt{2}} Ei$$

where $\Delta\phi'$ is the phase shift of the beam that interacted with the object.

After the beam passes through the Wollaston prism 52, two beams are formed in accordance with the following equations:

$E_1 = \frac{1}{2}Ei(1+\exp[i\pi/2+i\Delta\phi'])$ and $E_2 = \frac{1}{2}Ei(1-\exp[i\pi/2+i\Delta\phi'])$.

It should be apparent to those skilled in the art that if these two beams $E_1$ and $E_2$ are detected and measured by conventional differential analysis, that the phase shift information will be nulled and not available for further analysis.

Therefore, in accordance with the invention, detectors which are non-linear in detecting electric fields, such as photodiodes 54, 56 square the received electric field signals. The squared signals pass through respective R-C circuits. One circuit comprises resistor 58 and capacitor 60 connected to the cathode of photodiode 54, the other side of capacitor 60 being connected to one input of an isolation amplifier 66. The other side of resistor 58 is connected to a negative voltage potential. The anode of photodiode 54 is connected to ground potential. Similarly, the cathode of photodiode 56 is connected to one end of resistor 62 and one side of capacitor 64. The other end of resistor 62 is connected to a negative voltage potential. The other side of capacitor 64 is connected to the other input of isolation amplifier 66. The anode of photodiode 56 is connected to ground potential. The output of the amplifier 66 along conductor 68 contains a signal commensurate with the phase shift of the scattered energy beam as shown by the following equations:

$$S_{bf} = |E_1|^2 - |E_2|^2$$

or $$S_{bf} = P \sin(\Delta\phi') = \Delta\phi'$$

where P is the incident laser beam power. The system is calibrated by measuring the power at each photodiode which is equal to P/2.

It will be apparent to those skilled in the art that both beams entering the flow cell 48 traverse the identical optical paths commencing from laser 40, except within the flow cell. By traversing the same paths, greater noise rejection is achieved than in the heretofore known systems.

In the preferred embodiment described, a homodyne interferometer, i.e. the sample beam and reference beam are both at the same wavelength, is used because of the improvement in the signal to noise ratio and the reduced difficulty of obtaining Shot noise limited performance. A factor of two difference between a homodyne and a heterodyne system exists if only one of the upper or lower sideband signals is detected in the heterodyne system.

In an alternative embodiment, a dark field arrangement or Michelson system such as that shown in FIG. 1, is made using a heterodyne interferometer, i.e. the sample beam and reference beam have different wavelengths. Such a configuration permits the two arms of the interferometer to have different path lengths.

Figure 3:
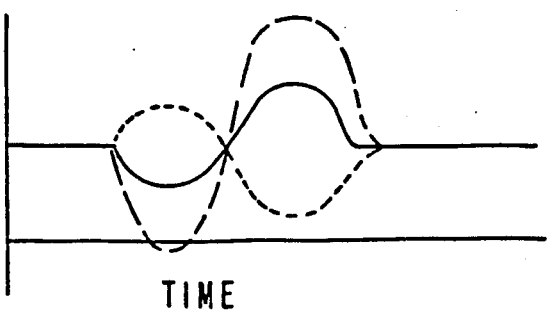
FIG. 3 is a graphical representation of one of the two detected signals.
Figure 4:
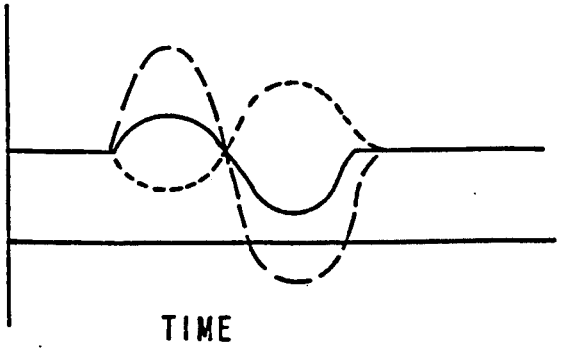
FIG. 4 is a graphical representation of the other detected signal.

Having described the method and apparatus for obtaining a detected signal at conductor 68, now an analysis of the signal must be performed in order to determine the characteristics of the object in the fluid. Referring to FIGS. 3 and 4, there are shown waveforms of detected signals at the photodiodes 54 and 56 respectively. The dotted line represents a bubble detected in the flow cell. The solid line represents a particle. The dashed line represents another particle. It should be observed that the phase of a bubble is opposite that of a particle having an index of refraction greater than the surrounding fluid, such as a solid particle. The amplitude of the signal is indicative of size or type of particle, i.e. metal, dielectric, bacteria or the like. Each particle type has an identifying signal signature. While the signals shown in FIGS. 3 and 4 have the same frequency, objects which are large compared to the beam diameter can generate signals of different frequencies.

In order to perform signal analysis, the detection circuit, including amplifier 66 is configured to provide a difference signal of the two detected signals such as is shown in FIG. 3 and FIG. 4. The result will be a bipolar signal which is easier to measure and detect as having either a positive or negative initial slope. With such information, a pulse analyzer can detect either a bubble or solid particle and the approximate size of each.

Figure 5:
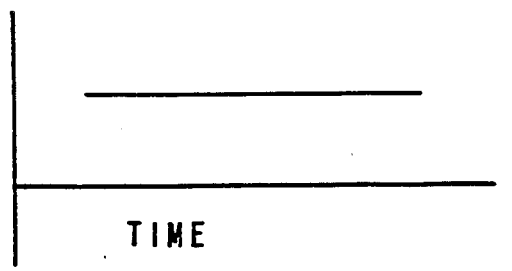
FIG. 5 is a graphical representation of the summation of the signals in FIG. 3 and FIG. 4 where the particle is a dielectric.
Figure 6:
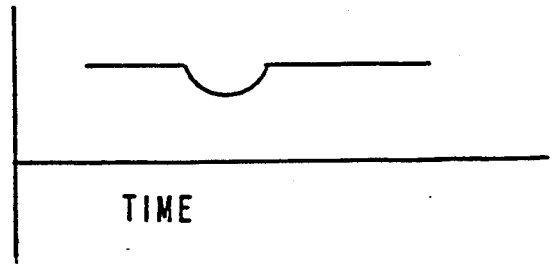
FIG. 6 is a graphic representation of the summation of the signals in FIG. 3 and FIG. 4 where the particle is a metal.

Another analysis method is to configure the detection circuit including amplifier 66 to provide the sum of the signals shown in FIG. 3 and FIG. 4 as is known to those skilled in the art. Experiments have shown that if a dielectric particle is detected, the resultant sum signal is a flat curve as shown in FIG. 5. If a metal particle is detected, the sum signal usually results in a dip as shown in in FIG. 6.

In order to perform the above analysis and other analysis, in addition to reconfiguring amplifier 66, the output signal along conductor 68 is converted to a digital signal by analog to-digital converter 70. The output of the converter 70 is then provided to a pulse analyzer for signal analysis as is known to those skilled in the art. The analyzer is capable of measuring waveform characteristics such as peak amplitude, frequency, slope and is also able to perform transform analysis of the signal. By analyzing the characteristics of the output waveform for such features as symmetry, number of positive and negative lobes, spacing of the lobes, the velocity and position of the trajectory of the detected scatterer can be computed with reference to the focused region. Such devices are known to those skilled in the art of signal processing and analysis.

Another requirement of a monitor detecting system is the ability to determine when there are more than a predetermined quantity of objects in the fluid larger than a predetermined size. In order to accomplish this feature, a variable threshold detector 72 is connected to the output of amplifier 66. Whenever a particle is detected of a size greater than a predetermined size, a pulse is provided along conductor 74 to a counter 76. Whenever the count in counter exceeds a predetermined quantity during a preset time interval, between being reset, an alarm signal is provided along conductor 78.

Figure 7:
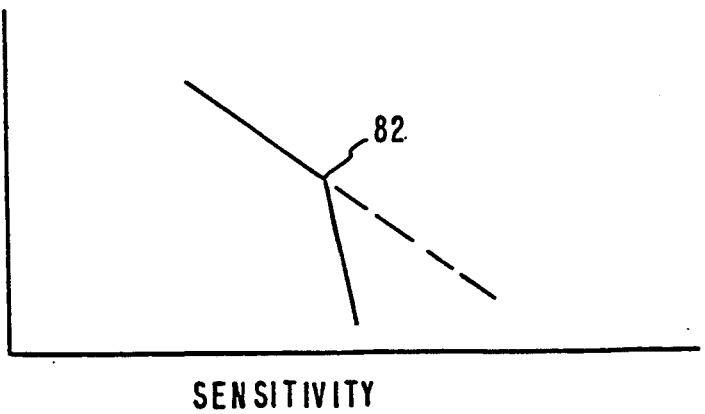
FIG. 7 is a graphical representation of the flow rate versus sensitivity.

Another advantage of the present system is that the sensitivity is Shot noise limited rather than Johnson noise limited. In FIG. 7, the solid line represents the sensitivity as a function of fluid flow in a conventional monitor. The first portion of the curve from left to right is the known shot noise limited curve, proportional to the sixth power of the particle size. After the knee 82, the curve is Johnson noise limited, proportional to the twelfth power of the particle size. Experimental results using the present system have shown that the sensitivity more closely follows the dashed line after the knee 82. That is, the system is shot noise limited and the Johnson noise limit has no effect.

Among the uses of the monitor detecting system is determining whether the fluid filters in the semiconductor processing system are functioning properly. When there is an increase in the quantity of particles detected or in the size of the particles detected, the fluid flow can be stopped, filters and lines inspected and the problem repaired. Also, if the analyzer detects bacteria or other undesirable particles in the processing fluid, the fluid flow can be stopped until the source is identified and corrected before continuing manufacture, thereby increasing yield.

There has been described an object monitor detector and a method of detecting objects in a fluid which is capable of distinguishing bubbles from particles in a fluid, detecting objects having indices of refraction close to that of the fluid and extending the sensitivity of the device for detecting objects to the one-tenth groundrule limit.

While there has been described and illustrated a preferred embodiment of an object monitor detector and a method of detecting objects in a fluid, it will be apparent to those skilled in the art that variations and modifications are possible without deviating from the broad scope of the invention which shall be limited solely by the scope of the appended claims.

What is claimed is:

1. An apparatus for detecting objects within a fluid comprising:
   means for transmitting a beam of optical energy;
   first optical means for splitting said beam of optical energy into two substantially parallel beams of different polarization, having axes which are laterally displaced and focused in a focal plane located where a fluid is to be inspected, which focal plane is substantially normal to the beam axes;
   second optical means for recombining said two beams into a single beam after said beams travel through the focal plane a distance greater than the depth of focus of said two beams;
   third optical means for separating said single beam into two beams, and
   detection means for receiving said two beams from said third optical means and providing a signal responsive to a phase shift between said two beams after traveling through the focal plane.

2. An apparatus as set forth in claim 1, wherein said first optical means and said second optical means includes Nomarski lenses.

3. An apparatus as set forth in claim 1, wherein said third optical means includes a Wollaston prism.

4. Apparatus as set forth in claim 1, wherein said first optical means and said second optical means include Nomarski lenses and said third optical means includes a Wollaston prism.

5. An apparatus as set forth in claim 1, wherein said third optical means spatially separates said single beam into beams separated by substantially 90 degrees.

6. An apparatus as set forth in claim 1, wherein said detection means is non-linear.

7. An apparatus as set forth in claim 1, wherein said detection means includes photodetectors and an isolation amplifier.

8. An apparatus as set forth in claim 1, wherein said two beams of different polarization are each polarized in a plane substantially normal to each other.

9. An apparatus as set forth in claim 1, further comprising analysis means for receiving said signal from said detection means and providing an output signal indicative of a characteristic of an object in the fluid.

10. An apparatus as set forth in claim 9, wherein said analysis means includes a counter for providing a signal indicative of a quantity of objects being detected during a predetermined time interval.

11. An apparatus as set forth in claim 9, wherein said characteristic is a type of object.

12. An apparatus as set forth in claim 9, wherein said characteristic is size of object.

13. An apparatus as set forth in claim 1, wherein said beam of optical energy is a laser beam.

14. An apparatus as set forth in claim 1, further including a flow cell disposed between said first optical means and said second optical means.

15. A method of detecting objects in a fluid comprising the steps of:
   transmitting a beam of optical energy;
   splitting said beam of optical energy into two substantially parallel beams of different polarization having axes which are laterally displaced and focussed in a focal plane located in a fluid to be inspected, which focal plane is substantially normal to the beam axes;
   recombining said two beams into a single beam after said beams travel through the focal plane a distance greater than the depth of focus of said two beams;
   separating said single beam into two beams, and
   detecting said separated two beams for providing a signal responsive to a phase shift of said two beams after traveling through said focal plane.

16. A method as set forth in claim 15, wherein each beam of said two beams of different polarization being polarized in a plane substantially normal to the other beam.

17. A method as set forth in claim 15, wherein said separating said single beam separates said single beam into two beams, spatially separated by substantially 90 degrees.

18. A method as set forth in claim 15, further including analyzing said signal responsive to a phase shift for providing a signal indicative of a characteristic of a detected object.

19. A method as set forth in claim 15, further including analyzing said signal responsive to a phase shift for providing a signal indicative of a quantity of objects detected during a predetermined time interval.

20. A method as set forth in claim 15, wherein said optical energy is laser energy.

21. An apparatus for detecting and analyzing object in a system for manufacturing semiconductor or other microelectronic devices comprising:
   a flow cell adapted to pass therethrough an object containing fluid;
   means for transmitting a beam of optical energy;
   first optical means for splitting said beam of optical energy into two substantially parallel beams of different polarization, having axes which are laterally displaced and focussed in a focal plane located in said flow cell, which focal plane is substantially normal to the beam axes;
   second optical means for recombining said two beams into a single beam after said beams travel through said flow cell;
   third optical means for spatially separating said single beam into two beams, and
   detection means for providing a signal responsive to a phase shift of said two beams from said third optical means.

22. An apparatus as set forth in claim 21, wherein said first optical means and said second optical means includes Nomarski lenses.

23. An apparatus as set forth in claim 21, wherein said third optical means includes a Wollaston prism.

24. An apparatus as set forth in claim 21, wherein said first optical means and said second optical means includes Nomarski lenses and said third optical means includes a Wollaston prism.

25. An apparatus as set forth in claim 21, wherein said spatially separated beams are separated by substantially 90 degrees.

26. An apparatus as set forth in claim 21, wherein said detection means is non-linear.

27. An apparatus as set forth in claim 21, wherein said detection means includes photodetectors and an isolation amplifier.

28. An apparatus as set forth in claim 21, wherein said two beams of different polarization are each polarized in a plane substantially normal to each other.

29. An apparatus as set forth in claim 21, further comprising analysis means for receiving said signals responsive to a phase shift and providing an output signal indicative of a characteristic of a detected object in the flow cell.

30. An apparatus as set forth in claim 29, wherein said analysis means includes a counter for providing an output signal indicative of a quantity of objects being detected during a predetermined time interval.

31. An apparatus as set forth in claim 29, wherein said characteristic is a type of object.

32. An apparatus as set forth in claim 29, wherein said characteristic is size of object.

33. An apparatus as set forth in claim 21, wherein said optical energy is laser energy.

34. In a system for manufacturing semiconductor or other microelectronic devices, a method for monitoring process fluids comprising the steps of:
passing a process fluid through a flow cell;
transmitting a beam of optical energy;
splitting said beam of optical energy into two substantially parallel beams of different polarization, having axes which are laterally displaced and focussed in a focal plane located in the flow cell, which focal plane is substantially normal to the beam axes;
recombining said two beams into a single beam after said beams travel through the flow cell;
spatially separating said single beam into two beams, and
detecting said spatially separated beams for providing a signal responsive to a phase shift of said two beams after traveling through the flow cell.

35. A method as set forth in claim 34, wherein each beam of said two beams of different polarization being polarized in a plane substantially normal to the other beam.

36. A method as set forth in claim 34, wherein said spatially separating said single beam separates said single beam into two beams spatially separated by substantially 90 degrees.

37. A method as set forth in claim 34, further including analyzing said signal responsive to a phase shift for providing an output signal indicative of a characteristic of a detected object.

38. A method as set forth in claim 34, further including analyzing said signal responsive to a phase shift for providing an output signal indicative of a quantity of objects detected during a predetermined time interval.

39. A method as set forth in claim 34, wherein said beam of optical energy is a beam of laser energy.

40. A method as set forth in claim 34, wherein said detecting includes non-linear detection.

41. An apparatus for inspecting a fluid comprising:
means including Nomarski objectives for transmitting into a fluid to be inspected two substantially parallel beams of optical energy, said beams being mutually coherent, of different polarizations, having axes which are laterally displaced and being focussed in a focal plane located where the fluid is to be inspected which focal plane is substantially normal to the beam axes;
detector means;
means for coherently interfering at said detector means said beams after passing through the focal plane a distance greater than the depth of focus of said beams, and
means for generating a signal commensurate with difference of phase between said beams.

42. An apparatus for inspecting a fluid comprising:
means for transmitting into a fluid to be inspected two substantially parallel beams of optical energy, said beams being mutually coherent, of different polarizations, having axes which are laterally displaced and being focussed in a focal plane located where the fluid is to be inspected which focal plane is substantially normal to the beam axes;
detector means;
means including Norarski objectives for coherently interfering at said detector means said beams after passing through the focal plane a distance greater than the depth of focus of said beams, and
means for generating a signal commensurate with difference of phase between said beams.

* * * * *